United States Patent [19]

Moynihan

[11] Patent Number: 5,693,336
[45] Date of Patent: *Dec. 2, 1997

[54] BLOOD STABLE LIPOSOMAL CYCLOSPORIN FORMULATIONS

[75] Inventor: Karen L. Moynihan, Brea, Calif.

[73] Assignee: NeXstar Pharmaceuticals, Inc., Boulder, Colo.

[*] Notice: The portion of the term of this patent subsequent to Jun. 30, 2000, has been disclaimed.

[21] Appl. No.: 475,294

[22] Filed: Jun. 7, 1995

[51] Int. Cl.$^6$ .......................... A61K 9/127; A61K 9/133
[52] U.S. Cl. ........................................................ 424/450
[58] Field of Search ............................................. 424/450

[56] References Cited

U.S. PATENT DOCUMENTS

| | | | |
|---|---|---|---|
| 4,608,211 | 8/1986 | Handjani | 24/4.6 |
| 4,663,167 | 5/1987 | Berostein | 514/37 |
| 4,692,433 | 9/1987 | Hostetler et al. | 514/12 |
| 4,797,285 | 1/1989 | Barenholz et al. | 424/450 |
| 4,812,312 | 3/1989 | Lopez-Berestein et al. | 424/417 |
| 4,895,719 | 1/1990 | Radhakrishnan et al. | 424/45 |
| 4,913,902 | 4/1990 | Kilpatrick et al. | 424/85.8 |
| 4,952,405 | 8/1990 | Young | 424/423 |
| 4,963,362 | 10/1990 | Rahman et al. | 424/450 |
| 5,000,887 | 3/1991 | Tenzel | 264/4.6 |
| 5,023,087 | 6/1991 | Yau-Young | 424/450 |

FOREIGN PATENT DOCUMENTS

| | | |
|---|---|---|
| 4402867 | 1/1994 | Denmark . |
| 0697214 | 2/1996 | European Pat. Off. . |
| WO 90/00389 | 1/1990 | WIPO . |
| WO 91/04019 | 4/1991 | WIPO . |
| 9218104 | 10/1992 | WIPO . |

OTHER PUBLICATIONS

Hsieh et al. "Preliminary Report: The Use of Liposome–Encapsulated Cyclosporin In a Rat Model Transplanation Proceedings", vol. XVII, pp. 1397–1400. (Feb., 1985).

Stuhne–Sekalec et al. "Encapsulation of Cyclosporine by Phosphatidylinositol–Cholesterol Liposomes", Transplantation vol. 41, pp. 659–660 (1986).

Stuhne–Sekalec et al. "Co–encapsulation of Cyclosporin and Insulin by Liposomes", J. Biochem. Biophys, Methods vol. 13, pp. 23–27(1986).

Gruber et al., "liposomal Formulation Eliminates Acute Toxicity and Pump Incompatibility of Parenteral Cyclosporin", Res. vol. 5, pp. 601–607 (1989).

Stuhne–Sekalec et al. "Liposomes as Cyclosporin A Carriers: Positively Charged . . . Phosphatidylinositol", J. Microencapsulation vol. 6, pp. 177–182 (1989).

Venkataram et a. "Pharmacokinetics of Two Alternative Dosage Forms for Cyclosporine: Liposomes and Intralipid" J. Pharm. Sci. vol. 79, pp. 216–219 (1990).

Stuhne–Sekalec et al. "Liposomes as Cyclosporin A Carriers: The Influence . . . Cyclosporin A", J. Microencapsulation vol. 8, pp. 283–294 (1991).

Stuhne–Sekalec et al. "Liposomes as Carriers of Cyclosporin A, J. Microencapsulation" vol. 8, pp. 441–446 (1991).

Stuhne–Sekalec et al. "Liposomes as Cyclosporin A Carriers: ESR Study . . . Phosphatidylglycerol Liposomes", J. Microencapsulation vol. 8, pp. 455–463 (1991).

Deamer: Liposome Prep. Chap. I, p. 27 (1983).

Szoke: Ann. Rev. Biophys. Bioeng. vol. 9, p. 467 (1980).

Van de Vrie, W., "In vitro and in vivo chemosensitizing effect of cyclosprpin A on an intrinsic multidrug–resistant rat colon tumour", Cancer Research Clinical Oncology vol. 119, pp. 609–614 (1993).

Freise, Chris E., "The increased efficacy and decreased nephrotoxicity of a cyclosporine liposome Transplantation" vol. 57, No. 6, pp. 928–932 (Mar. 1994).

Sonneveld, P. "Clinical modulation of multidrug resistance in multiple myeloma; Effect of cyclosporin on resistant tumor cells", Journal of Clinical Oncology vol. 12, No. 8, pp. 1584–1591 (Aug. 1994).

Colombo, Tina, "Cyclosporin a markedly changes the distribution of doxorubicin in mice and rats The Journal of Pharmacology and Experimental Therapeutics", vol. 269, No. 1, pp. 22–27 (1994).

Yano, Seiji, "Cyclosporin a enhances susceptibility of multi–drug resistant human cancer cells to anti–P–glycoprotein antibody–dependent cytotxicity of monocytes, but not of lymphocytes", J. Cancer Res. vol. 85, pp. 194–203 (Feb. 1994).

van der Graaf, Winette T.A., "Effects of amiodarone, cyclosporin A, and PSC 833 on the cytotoxicity of mitoxantrone, doxorubicin and vincristine in non–P–glycoprotein human small cell lung cancer cell lines", Cancer Research vol. 54, pp. 5268–5373 (Oct. 15, 1994).

Erlichman, Charles, "Phase I pharmacokinetic study of cyclosporin a combined with doxorubicin Cancer Research" vol. 53, pp.4837–4842 (Oct. 15, 1993).

Sonneveld, Pieter, "Modulation of multidrug–resistant multiple myeloma by cyclosporin", The Lancet vol. 340, No. 8814, pp. 255–259 (Aug. 1, 1992).

(List continued on next page.)

*Primary Examiner*—Gollamudi S. Kishore
*Attorney, Agent, or Firm*—NeXstar Pharmaceuticals, Inc.

[57] ABSTRACT

An improved liposomal cyclosporin therapeutic formulation, comprising phosphatidylcholine, cholesterol, dimyristoylphosphatidylglycerol and a cyclosporin in a mole ratio of about 28:1:3:1 to 40:1:3:1 which are stable in mammalian blood.

9 Claims, No Drawings

OTHER PUBLICATIONS

Samuels, Brian L., "Modulation of vinblastine resistance with cyclosporine; A phase I Study", Clinical Pharmacology & Therapeutics vol. 54, No. 4, pp. 421–429 (Oct. 1993).

Sikic, Branimir I., "Modulation of multidrug–resistance: At the Threshold", Journal of Clinical Oncology vol. 11, No 9, pp. 1629–1635 (Sep. 1993).

Thierry, Alain R., "Effect of liposomes on P–glycoprotein function in multidrug–resistant cells", Biochemical and Biophysical Research Communications vol. 187, No. 2, pp. 1098–1105 (Sep. 16, 1992).

Rahman, Aquilur, "Liposome–mediated modulation of multidrug resistance in human HL–60 leukemia cells", Journal of the National Cancer Institute vol. 84, No. 24, pp. 1909–1915 (Dec. 16, 1992).

Dalton, William S., "Drug resistance modulation in the laboratory and the clinic", Seminars in Oncology vol. 20, No. 1, pp. 64–69 (Feb. 1993).

Clynes, Martin, "Cellular models for multiple drug resistance in cancer", In Vitro Cell. Dev. Biol. 29A, pp. 171–179 (Mar. 1993).

Dietel, Manfred, "Second International symposium on cytostatic drug resistance", Cancer Research vol. 53, pp. 2683–2688 (Jun. 1, 1993).

Twentyman, Peter R., "A possible role for cyclosporins in cancer chemotherapy", Anticancer Research vol. 8, pp. 985–994 (1988).

List, Alan F., "Phase I/II trial of cyclosporine as a chemotherapy resistance modifier in acute leukemia", Journal of Clinical Oncology vol. 11, No. 9, pp. 1652–1660 (Sep. 1993).

Boesch, Danielle, "In vivo circumvention of P–glycoprotein–mediated multidrug resistance of tum cells with SDZ PSC 833", Cancer Research vol. 51, pp. 4226–4233 (Aug. 15, 1991).

Yahanda, Anne M., "Phase I trial of etoposide with cyclosporine as a modular of multidrug resistance", Journal of Clinical Oncology vol. 10, No. 10, pp. 1624–1634 (Oct. 1992).

Benedicte Jachez, Rene, "Restoration of taxol sensitivity of multidrug resistant cells by the cyclosporine SDZ PSC 833 and the cyclopeptolide SDZ 280–466", Journal of the National cancer Institute vol. 85, No. 6, pp. 478–483 (Mar. 17, 1993).

Slater, Lewis M., "Cyclosporin a reverses vincristine and daunorubicin resistance in acute lymphatic leukemia in vitro", Cyclosporin A Corrects Vincristine and Daunorubicin Resistance vol. 77, pp. 1405–1408 (Apr. 1986).

Friche, Ellen, "Comparison of cyclosporin A and SDZ PSC 833 as multidrug resistance modulators in a daunorubicin resistant Ehrlich ascites tumor", Cancer Chemotherapy and Pharmacology vol. 30, pp. 235–237 (1992).

Shoji, Y, "Verapamil and cyclosporin A modulate doxorubicin toxicity by distinct mechanisms", Cancer Letters vol. 57, p. 209–218 (1991).

Hu, Xiu F., "Combined use of cyclosporin A and verapamil in modulating multidrug resistance in human leukemia cell lines", Cancer Research vol. 50, pp. 2953–2957 (May 15, 1990).

Meador, Josephine, "Enhancement by cyclosporin A of daunorubicin efficacy in Ehrilich aacites carcinoma and murine hepatoma 129", Cancer Research vol. 47, pp. 6216–6219 (Dec. 1, 1987).

Kuhl, Jorn–Sven, "Use of etoposide in combination with cyclosporine for purging multidrug resistant leukemic cells from bone marrow in a mouse model", Advances in Bone Marrow Purging and Processing, pp. 25–34 (1992).

Nygren, P. "Verapamil and cyclosporin a sensitize human kidney tumor cells to vincristine in absence of membrane P–glycoprotein and without apparent changes in the cytoplasmic free $Ca^{2+}$ concentration", Bioscience Reports vol. 10, No. 2, pp. 231–237, (1990).

Twentyman, P.R., "Chemosensitisantion by verapamil nd cyclosporin A in mouse tumour cells expressing different levels of P–glycoprotein and CP22 (Sorcin)", Cancer vol. 62, pp. 89–95 (1990).

Saeki, Tohru, "Human P–glycoprotein transports cyclosporin A and FK506", The Journal of Biological Chemistry vol. 268, No. 9, pp. 6077–6080 (Mar. 25, 1993).

Gilbert et al., Characterization and Administration of Cyclosporin Liposomes as a Small–Particle Aerosol, Chemical Abstrats, vol. 120, No. 14, 4 Apr. 1994, Columbus, Ohio, US, Abstract No. 173337g.

BLOOD STABLE LIPOSOMAL CYCLOSPORIN FORMULATIONS

FIELD OF THE INVENTION

This invention relates to the fields of biochemistry and medicine, and in particular to a novel liposomal formulation and process. More specifically, it relates to a liposomal formulation containing the immunosuppressive agent cyclosporine and to its process of manufacture. This invention also relates to a liposomal cyclosporine formulation having reduced toxicity and increased stability in the blood of mammals.

BACKGROUND OF THE INVENTION

The cyclosporins were discovered in 1970 by researchers in attempts to identify new antimicrobial agents. Cyclosporine (also known as cyclosporin A), a potent immunosuppressive agent, was isolated from two strains of imperfect fungi, *Cylindrocapon lucidum* Booth and *Tolypocladium inflatum* Gams.

Cyclosporins are hydrophobic, neutral, cyclical peptides which have essentially similar chemical and physical characteristics. Cyclosporine is a representative example, and consists of eleven amino acids with a total molecular weight of 1201. Cyclosporine is soluble in methanol, chloroform and ether and essentially insoluble in water. It is supplied for therapeutic purposes as either an intravenous preparation dissolved in a proprietary castor oil and alcohol, or an oral formulation dissolved in Labrophil and olive oil.

Cyclosporine is primarily used for treating allograft patients and has been used in experimental trials for autoimmune diseases. The use of this drug has greatly increased the survival ate of transplant patients since its advent in 1978.

Although cyclosporine is a very useful immunosuppressive agent, it can also be highly toxic when used for prolonged periods of time and/or at high doses, both of which are necessary to ensure graft acceptance. The most severe side effect associated with cyclosporine therapy is drug-induced nephrotoxicity. Vascular interstitial toxicity is the most common form of cyclosporine nephrotoxicity and can manifest itself as three different morphological lesions, occurring either alone or in combination. Although not all of these morphological changes associated with cyclosporine nephrotoxicity are unique to cyclosporine toxicity, if they are observed in combination with one another and there is also a corresponding high level of serum cyclosporine, the damage is probably a result of cyclosporine toxicity. Some individuals may show some of these adverse reactions at therapeutic doses (5 to 10 mg/kg/day) which produce trough levels of 200–500 ng/ml in whole blood and 20–60 ng/ml in serum. Renal toxicities can be monitored serologically by following the increase in creatinine levels. The increase in creatinine level is probably a direct result of arteriole constriction and blockage which would result in lower glomerular filtration rate and thus an increase in serum creatinine.

There are other adverse side reactions associated with cyclosporine treatment. These occur with varying frequencies depending on the type of transplant. They include symptoms, such as cardiovascular hypertension and cramps, skin hirsutism, gum hyperplasia, diarrhea, nausea, vomiting, hepatotoxicity, hematopoietic alterations including leukopenia and lymphoma, respiratory distress and sinusitis.

Other side effects associated with the intravenous delivery of cyclosporine are due to the intravenous carrier vehicle, Cremophor -El (CreL). CreL is a polyoxyethylated castor oil that is one of the best ionic surfactants used to dissolve lipophilic drugs. The most common of the adverse reactions associated with CreL administration has been anaphylaxis which results from a rapid release of histamine and causes increasing hypertension. It is also believed that part of the nephrotoxicity associated with cyclosporine treatment may be enhanced by CreL deposition and crystal formation within the kidney tubules. Other studies have also shown a decrease in both renal blood flow and creatinine clearance in animals treated with CreL. Riconic acid, a component of CreL, has been shown to cause vasoconstriction which could also be linked to hypertension and decreased glomerular blood flow.

Efforts have been made to eliminate the toxicity of cyclosporine by incorporating the drug into liposomes for purposes of administration, thus eliminating the toxic castor oil vehicle. Liposomes are microscopic delivery vesicles made, in part, from phospholipids which form closed, fluid filed spheres when mixed with water. Phospholipid molecules are polar, having a hydrophilic ionizable head, and a hydrophobic tail consisting of long fatty acid chains. Thus, when sufficient phospholipid molecules are present with water, the tails spontaneously associate to exclude water while the hydrophilic phosphate heads interact with water. The result is a bilayer membrane in which the fatty acid tails converge in the newly formed membrane's interior and the polar heads point in opposite directions toward an aqueous medium. The polar heads at one surface of the membrane point toward the aqueous interior of the liposome. At the opposite surface, the polar heads interact with the surrounding aqueous medium. As the liposomes form, water soluble molecules will be incorporated into the aqueous interior, and lipophilic molecules will tend to be incorporated into the lipid bilayer. Liposomes may be either multilamellar, like an onion with liquid separating many lipid bilayers, or unilamellar, with a single bilayer surrounding an entirely liquid center.

There are many types of liposome preparation techniques which may be employed and which produce various types of liposomes. These can be selected depending on the use, the chemical intended to be entrapped, and the type of lipids used to form the bilayer membrane.

Those parameters which must be considered in producing an optimal liposome preparation are similar to those of other controlled release mechanisms. They are as follows: (1) high percent of chemical entrapment; (2) increased chemical stability; (3) low chemical toxicity; (4) rapid method of production; and (5) reproducible size distribution.

The first method described to encapsulate chemicals in liposomes involved production of multilamellar vesicles (MLVs). The MLV process involves dissolving the lipid components in a suitable solvent, evaporation of the solvent to form a dry lipid film, and hydration of the lipid film with an aqueous medium. The multilamellar vesicles which form are structures having generally more than three concentric bilayers. Lipophilic drugs are incorporated into the MLVs by codissolution of the drugs in the solvent phase, while hydrophilic drugs are entrapped between the bilayers with the hydration buffer. By increasing the length of time of hydration and gentle shaking of the resuspending lipid film, one can achieve a higher proportion of the aqueous phase per mole of lipid, and thus enhance hydrophilic drug encapsulation. The increased entrapment of aqueous buffer can also be achieved by using charged lipids.

Liposomes can also be formed as unilamellar vesicles (UVs), which have diameters up to 2 μm, but generally less than 1 μm.

There are several techniques which are used to produce unilamellar liposomes. Large unilamellar vesicles (LUVs) can be formed using the reverse-phase evaporation method. This is done by removing the organic phase of a sonicated emulsion of phospholipid, buffer and excess organic solvent under pressure. This technique is especially useful for encapsulating large volumes of aqueous phase containing hydrophilic molecules, such as ferritin, 25S RNA or SV-40 DNA. Maximum encapsulation of the LUV aqueous phase (65%) can be obtained if the ionic strength of the aqueous buffer is low (0.01M NaCl); encapsulation decreases to 20% as the ionic strength is increased to 0.5M NaCl. The size of the LUVs varies with the lipid and cholesterol content. Vesicles formed from cholesterol and phospholipid with a 1:1 mole ratio, form a heterogeneous size distribution of vesicles with a mean diameter, based upon entrapped volume, of 0.47 µm and a size range of 0.17–0.8 µm Vesicles prepared from similar phospholipid mixtures lacking cholesterol have a mean size of 0.18 µm and a size range of 0.1–0.26 µm.

The solvent infusion evaporation method can produce both larger or smaller UVs, depending on variations in the technique. To form larger UVs, phospholipids are dissolved in diethylether and injected into a buffer maintained at 55°–65° C. containing the material to be entrapped or injected. The mixture is kept under vacuum at 30° C. When the solvent has evaporated, vesicles are formed. The range in diameter of these vesicles is from 0.25–1 µm. This procedure is well suited for entrapment for large molecules.

Smaller unilamellar vesicles can also be formed using a variety of techniques. By dissolving phospholipids in ethanol and injecting them into a buffer, the lipids will spontaneously rearrange into unilamellar vesicles. This provides a simple method to produce UVs which have internal volumes similar to that of those produced by sonication (0.2–0.5 L/mol/lipid). Sonication or extrusion (through filters) of MLVs also results in dispersions of UVs having diameters of up to 0.2 µm, which appear as clear or translucent suspensions.

Another common method for producing small UVs is the detergent removal technique. Phospholipids are solubilized in either ionic or non-ionic detergents such as cholates, Triton X, or n-alkylglucosides. The drug is then mixed with the solubilized lipid-detergent micelles. Detergent is then removed by one of several techniques: dialysis, gel filtration, affinity chromatography, centrifugation, or ultrafiltration. The size distribution and entrapment efficiencies of the UVs produced this way will vary depending on the details of the technique used. Also when proteins are entrapped, there is no certainty that once the detergent has been removed, the protein will renature into its native bioactive conformation.

The therapeutic use of liposomes includes the delivery of drugs which are normally very toxic in the free form. In the liposomal form the toxic drug may be directed away from the sensitive tissue and targeted to selected areas. Liposomes can also be used therapeutically to release drugs slowly, over a prolonged period of time, reducing the frequency of administration. In addition, liposomes can provide a method for forming an aqueous dispersion of hydrophobic drugs for intravenous delivery.

When liposomes are used to target encapsulated drugs to selected host tissues, and away from sensitive tissues, several techniques can be employed. These procedures involve manipulating the size of the liposomes, their net surface charge as well as the route of administration. More specific manipulations have included labeling the liposomes with receptors or antibodies for particular sites in the body.

The route of delivery of liposomes can also affect their distribution in the body. Passive delivery of liposomes involves the use of various routes of administration e.g., intravenous, subcutaneous and topical. Each route produces differences in localization of the liposomes. Two common methods used to actively direct the liposomes to selected target areas are binding either antibodies or specific receptor ligands to the surface of the liposomes. Antibodies are known to have a high specificity for their corresponding antigen and have been shown to be capable of being bound to the surface of liposomes, thus increasing the target specificity of the liposome encapsulated drug.

Since the chemical composition of many drugs precludes their intravenous administration, liposomes can be very useful in adapting these drugs for intravenous delivery. Many hydrophobic drugs, including cyclosporine, fall into this category because they cannot be easily dissolved in a water-based medium and must be dissolved in alcohols or surfactants which have been shown to cause toxic reactions in vivo. Liposomes, composed of predominantly lipids, with or without cholesterol, are nontoxic. Furthermore, since liposomes are made up of amphipathic molecules, they can entrap hydrophilic drugs in their interior space and hydrophobic molecules in their lipid bilayer.

In prior applications, it was shown that liposome encapsulated cyclosporin can be formulated having high entrapment characteristics along with good stability; U.S. application Ser. No. 07/687,812 and U.S. application Ser. No. 08/417,487, both incorporated herein by reference. These formulations were also shown to be efficacious in suppressing immune response in the cells of mammals and reducing multiple drug resistance of cancer cells. Liposomal formulations are described in U.S. application Ser. No. 08/472,635, entitled "LIPOSOMAL CYCLOSPORIN FORMULATIONS AS AGENTS FOR IMMUNOSUPPRESSIVE AND MULTIPLE DRUG RESISTANT INDICATIONS", filed on Jun. 7, 1995.

In a drive to develop a formula that is both safe and effective, such as required by such agencies as the Food and Drug Administration, it is desirable to provide formulations that have long shelf life stability. Unilamellar liposomes in many cases tend to aggregate and become larger over time. This is one parameter that indicates that the liposomes are not stable. Of course other parameters indicate unstable liposomes such as drug loss over time (leakage).

Thus, for a variety of reasons, having to do primarily with the inability of those of ordinary skill to entrap sufficient cyclosporins in a stable liposomal carrier, a therapeutically effective cyclosporin intercalated liposome product has not been commercially available. It has thus been a desideratum to develop a liposomal cyclosporin containing a formulation which enables a high proportion of the active agent to be incorporated therein, and which is sufficiently stable on the shelf and in the blood of mammals. This invention provides such a product.

It is also desirable to provide for a formulation that offers an optimum therapeutic index, that is, the right combination of high effectiveness and low toxicity. This high therapeutic value can be obtained when the formulation has the proper pharmacological profile based on attainable pharmacokinetics. Such liposomes are those that are found not only to be safe and efficacious, but are those that are stable in the blood of mammals.

Thus, an object of the present invention is to provide an improved liposome encapsulated cyclosporin formulation that has superior shelf life stability. It is also an object of the present invention to provide for a liposomal cyclosporin formula which is resistant to the loss of drug in the presence of whole (mammal) blood.

SUMMARY OF THE INVENTION

An improved liposomal encapsulated cyclosporin formulation is provided that is stable upon injection into the blood stream of a mammal, preferably a human. Also provided is a liposome encapsulated cyclosporin which provides for a cyclosporin which associates to a significant degree with a liposomal/plasma fraction (vs. cell fraction) of blood as a function of time. Liposomes having these properties are comprised of phosphatidylcholine, cholesterol, dimyristoylphosphdatidylglycerol and cyclosporin. These liposomes are unilamellar and have a size less than 75 nanometers and are stable in whole mammal blood. Further provided are liposomes having increased therapeutic indices.

The liposomes of the invention as practiced herein are generally prepared by (a) dissolving (i) a phosphatidylcholine, (ii) a cholesterol, (iii) dimyristoylphosphatidylglycerol, and (iv) a cyclosporin in an organic solvent to form a solution wherein the molar ratio of (i):(ii):(iii):(iv) ranges from about 28–40:1:3:1, (b) drying the organic solution thus formed to form a solid phase, e.g. a film or powder, (c) hydrating the solid phase with an aqueous solution having a pH from about 4.5 to about 9.5 to form stable liposomal cyclosporin therapeutic formulations having a mean particle size of less than 100 nm.

The invention provides a cyclosporine intercalated liposomal formulation which is stable on storage, contains a therapeutically effective amount of active ingredient, provides a liposomal cyclosporine formulation having reduced toxicity, and provides a liposomal formulation which is stable in whole blood. Whole blood stability is defined as having ≧70% of cyclosporin in a plasma/liposomal fraction at four hours and where <0.5 mg/ml of hemoglobin is released from red blood cells (RBC) to the plasma/liposome fraction at four hours as determined using a modified version of Sigma's Drabkin assay kit. This test shows an improvement of lower concentration hemoglobin released in whole mammal blood of 10-fold to over 200-fold improvement over cyclosporine in cremophor EL.

The hypothesis is that any cyclosporin which is loosely associated with the liposomes would be available to interact with cyclophilin receptors in red blood cell membranes causing RBC lysis and higher concentration of Hemoglobin release and higher cyclosporin in the plasma fraction. Although not being bound to any particular theory, it is hypothesized that the result of this interaction could be manifested as membrane leakiness causing loss of hemoglobin from the red cells to the plasma fraction at quantifiable levels.

DETAILED DESCRIPTION OF THE INVENTION

As used herein, the term liposome refers to unilamellar vesicles or multilamellar vesicles such as are described in U.S. Pat. Nos. 4,753,788 and 4,935,171, the contents of which are incorporated herein by reference. The term encapsulation, as used herein, refers to the incorporation of the cyclosporin into the liposome membrane.

Generally, the process of preparing the formulation embodied in the present invention is initiated with the preparation of a solution from which the liposomes are formed. This is done by weighing out a quantity of phosphatidylcholine, cholesterol, a phosphatidylglycerol and cyclosporin, preferably cyclosporin A, and dissolving them into an organic solvent, preferably chloroform and methanol in a 1:1 mixture. The solution is evaporated to form a solid lipid phase such as a film or powder, for example, with a rotary evaporator, spray dryer or other means. The film or powder is then hydrated with an aqueous solution having a pH ranging from about 4.5 to about 9.5 to form a liposome dispersion. The preferred aqueous solution for purposes of hydration is a buffered solution such as 9% sucrose/10 mM succinate or 10 mM phosphate buffer. The preferred buffer is 9% sucrose, 10 mM succinate wherein the pH is about 6.5. The lipid film or powder dispersed in buffer is heated from about 25° C. to about 65° C., preferable at about 55° C.

Multilamellar liposomes are formed by agitation of the dispersion, preferably through the use of a thin-film evaporator apparatus such as is described in U.S. Pat. No. 4,935,171 or through shaking or vortex mixing. Unilamellar vesicles are formed by the application of a shearing force to an aqueous dispersion of the lipid solid phase, e.g., by sonication or the use of a homogenizing apparatus such as a Gaulin homogenizer or a French press. Shearing force can also be applied using ether injection, freezing and thawing, dialyzing away a detergent solution from lipids, or other known methods used to prepare liposomes. The size of the liposomes can be controlled using a variety of known techniques including the duration of shearing force. Preferably, the modified Gaulin homogenizing apparatus described in U.S. Pat. No. 4,753,788 is employed to form unilamellar vesicles having diameters of less than 200 nanometers at a pressure of 3,000 to 10,000 psi and a temperature of about the aggregate transition temperature of the lipids. Methods for the agitation or shearing of lipids to form multilamellar or unilamellar vesicles are known in the art and are not part of this invention per se.

Distearoylphosphatidylcholine (DSPC), egg phosphatidylcholine (egg PC), hydrogenated egg phoshatidylcholine (HEPC) and hydrogenated soy phosphatidylcholine (HSPC) are the preferred phosphatidylcholines for use in the invention. The most preferred phosphatidylcholine is HSPC. Other suitable phosphatidylcholines include those obtained from soy beans or other plant sources, or those that are partially or wholly synthetic, such as dipalmitoylphosphatidylcholine. All of these are commercially available.

DMPG is the preferred negatively charged lipid for use in the invention. Other negatively charged lipids are suitable for use such as dilaurylphosphatidylglycerol (DLPG), dipalmitoylphosphatidylglycerol (DPPG), and dimyristoylphosphatidicacid (DMPA). All of these are also commercially available.

The preferred cyclosporin for use in the invention is cyclosporine (CSA). The preferred ratios of PC:chol:PG:CSA is from 28:1:3:1 to 40:1:3:1. The preferred formulas are PC:chol:DMPG:CSA wherein the PC is HSPC and the molar ratios are: 28:1:3:1, 30:1:3:1, 32:1:3:1, 34:1:3:1, 35:1:3:1, 36:1:3:1, and 40:1:3:1.

The preferred size of the liposomes is below 50 nm. The preferred percent entrapped cyclosporin is about 85% or greater.

This invention will be more fully understood by reference to the following examples, which are intended to be illustrative of the invention, and not limiting thereof.

EXAMPLE 1

Lipid films or spray dried powder containing various mole ratios of lipids and CSA as shown in Tables 1 and 2 were prepared. For the formulations shown in Table 1, DSPC was used. For the formulations shown in Table 2, HSPC was used. The formulations contained DSPC, cholesterol, DMPG and cyclosporine A. The spray dried powder or lipid films were hydrated with an aqueous buffer containing 9% sucrose in 10 mM succinate at pH 6.5 and heated to 55° C. and dispersed. This mixture was further hydrated in a water bath at 55° C. with stirring for 30 minutes. Shear force was applied at temperatures above the transition temperature of the formulation with a modified Gaulin homogenizer (Gamble U.S. Pat. No. 4,753,788) at 4,000–12,000 psi to generate unilamellar liposomes having average median diameters (Microtract) as shown in Table 1. Samples were filtered at 50°–65° C. through a 0.22 μm filter, composed of cellulose acetate.

TABLE 1

DSPC Based Liposomal Cyclosporin Formulations

| DSPC Based Formulations (DSPC:cholesterol:DMPG:CSA) | Average Median Diameter (nm) |
| --- | --- |
| 40:1:1:2 | 44.3 |
| 50:1:5:2 | 39.7 |
| 40:1:5:2 | 33.9 |
| 20:0.25:3:2 | 29.9 |
| 40:1:2:1.5 | 34.3 |
| 20:0.5:3:1.5 | 30.1 |
| 50:1:3:1 | 37.0 |
| 45:1:3:1 | 39.0 |
| 40:1:3:1 | 33.4 |
| 35:1:3:1 | 42.2 |
| 30:1:3:1 | 29.9 |
| 40:1:5:1 | 33.3 |
| 35:1:5:1 | 30.2 |
| 30:1:5:1 | 27.6 |
| 35:1:3:1 | 42.2 |
| 30:1:3:1 | 29.9 |
| 20:0.5:3:1 | 29.1 |
| 24:1:3:1 | 28.5 |
| 24:1:3:0.8 | 27.0 |
| 24:1:3:0.5 | 23.9 |
| 24:1:3:0.25 | 23.2 |
| 24:1:3:0.1 | 22.2 |

TABLE 2

HSPC Based Liposomal Cyclosporin Formulations

| HSPC Based Formulations (HSPC:cholesterol:DMPG:CSA) | Average Median Diameter (nm) |
| --- | --- |
| 20:0.5:3:1.5 | 29.0 |
| 35:1:5:1 | 39.8 |
| 20:0.5:3:1 | 30.1 |
| 40:1:3:1 | 62.1 |
| 36:1:3:1 | 33.1 |
| 34:1:3:1 | 37.1 |
| 32:1:3:1 | 35.1 |
| 30:1:3:1 | 38.1 |
| 28:1:3:1 | 31.4 |
| 26:1:3:1 | 34.1 |
| 24:1:3:1 | 34.2 |
| 24:1:3:0.8 | 30.1 |
| 24:1:3:0.67 | 31.0 |
| 24:1:3:0.5 | 29.7 |
| 24:1:3:0.25 | 25.7 |

EXAMPLE 2

The protocol for ascertaining the percent of CSA remaining in the plasma/liposome fraction after incubation with rat whole blood is described below. Each liposomal cyclosporin formulation was analyzed by HPLC to determine the concentration of CSA. Rat (Fischer, male) whole blood was obtained via cardiac puncture and collected into tubes containing EDTA as an anticoagulant. To ensure that hemolysis and/or cell damage has not occurred from the phlebotomy, for each tube of blood collected a small aliquot was centrifuged at 10,000 rpm for 5 minutes in a Brinkmann Eppendorf 5415 centrifuge. The red blood cells formed a pellet at the bottom of the tube and the plasma remained in a separate layer above the red blood cells after treatment. The plasma fraction was examined for color. If the plasma color was straw yellow to light pink, the vial of whole blood was determined to be acceptable and used in the assay. If the plasma color was bright red it was determined that hemolysis had occurred and the affected tube of blood was discarded. The whole blood tested was pooled to collect the appropriate volume of blood needed to complete the assay.

To each ml of whole rat blood, 0.6 mls of a cyclosporin containing liposome formulation was added to mimic an equivalent dose of 80 mg/kg in rats (1.7–2.0 mg/ml CSA). The exact amount of drug introduced (100% recovery) was calculated ([CSA] mg/ml *0.6 ml). The samples were immediately vortexed for approximately 10 seconds and incubated in a water bath at 37° C. for 4 hours. After the incubation was complete each sample was vortex mixed again for about 10 seconds and centrifuged at 10,000 rpm for 5 minutes in a Brinkmann Eppendorf 5415 centrifuge. The top plasma layer was removed and transferred via a glass Pasteur pipette to a test tube and the exact volume of plasma was recorded. An aliquot of the plasma was then assayed for CSA by a HPLC. The CSA content was then calculated for the plasma/liposome fraction ([CSA] mg/ml in plasma * plasma volume(ml)/mg total CSA added* 100) and was expressed as a percent of CSA recovered. The results are displayed in Table 3. It should be noted that 10–12% of the plasma volume was occluded in the red blood cell pellet and therefore not recoverable. The data presented in Table 3 was not corrected for the occluded volume such that the maximal percent of CSA recovered was at most 88–90%

TABLE 3

% CSA Detected in the Plasma Fraction After Fours Hours

| Liposomal Cyclosporin Formulation (PC:Chol:DMPG:CSA) | Type of PC | Sonicated or Homogenized | % CSA in Plasma/Liposome Fraction at 4 Hours |
| --- | --- | --- | --- |
| 26:1:3:1 | HSPC | homogenized | 64 |
| 28:1:3:1 | HSPC | homogenized | 79 |
| 30:1:3:1 | HSPC | homogenized | 90 |
| 32:1:3:1 | HSPC | homogenized | 85 |
| 34:1:3:1 | HSPC | homogenized | 87 |
| 36:1:3:1 | HSPC | homogenized | 84 |
| 40:1:3:1 | HSPC | sonicated | 90 |
| 35:1:5:1 | HSPC | sonicated | 53 |
| 24:1:3:1 | HSPC | sonicated | 47 |
| 24:1:3:0.8 | HSPC | sonicated | 44 |
| 24:1:3:0.67 | HSPC | sonicated | 46 |
| 24:1:3:0.5 | HSPC | sonicated | 71 |
| 19:3:1 | DSPC | sonciated | 45 |
| 20:0.25:3:2 | DSPC | sonciated | 27 |
| 35:1:5:1 | DSPC | sonciated | 53 |
| 30:1:5:1 | DSPC | sonciated | 50 |
| 20:0.5:3:1 | DSPC | sonciated | 36 |
| 24:1:3:1 | DSPC | sonciated | 40 |
| 24:1:3:0.8 | DSPC | sonciated | 60 |
| 20:0.5:3:1.5 | DSPC | sonciated | 33 |
| 35:1:3:1 | DSPC | sonciated | 87 |
| 40:1:3:1 | DSPC | sonciated | 85 |
| 30:1:3:1 | DSPC | sonciated | 64 |

EXAMPLE 3

Hemoglobin Release Test

It is desirable to develop a liposomal formulation of cyclosporin A that is stable and does not lose its active ingredient when introduced to whole blood. A hemoglobin release test was developed to screen candidate liposomal formulations containing cyclosporine A. The assay involved quantitating the amount of hemoglobin (an indicator of red blood cell lysis or damage) present in a plasma fraction after incubation of rat whole blood with liposomal formulations of cyclosporin A at 37° C. for 0, 1 or 4 hours followed by centrifugation at 10,000 rpm for 5 minutes.

The amount of hemoglobin released is related to the amount of loosely associated cyclosporin A in the liposomal formulations. A modified version of Sigma's Drabkin assay kit, which converts all oxidation species of hemoglobin to cyanomethemoglobin prior to quantitation, was used for the determination of total hemoglobin concentration in plasma.

The protocol for performing the hemoglobin release test is described below. Rat (Fischer, male) whole blood was obtained via cardiac puncture and collected into tubes containing EDTA as an anticoagulant. To ensure hemolysis and/or cell damage has not occurred from the phlebotomy, for each tube of blood collected a small aliquot was centrifuged at 10,000 rpm for 5 minutes in a Brinkmann Eppendorf 5415 centrifuge. The red blood cells formed a pellet at the bottom of the tube and the plasma remained in a separate layer above the red blood cells after subjection to this treatment. The plasma fraction was examined for color. If the plasma color was straw yellow to light pink the vial of whole blood was acceptable and used in the assay. If the plasma color was bright red hemolysis had occurred and the affected tube of blood was discarded. Whole blood was tested as previously described, and was pooled to collect the appropriate volume of blood needed to complete the entire assay.

To each ml of whole rat blood, 0.6 mls of a cyclosporin containing liposome formulation is added to mimic an equivalent dose of 80 mg/kg in rats (1.7–2.0 mg/ml CSA). A control sample is prepared with 1 ml of whole blood alone which is subjected to all the subsequent steps of the assay. The samples are immediately vortexed for 10 seconds and incubated in a water bath at 37° C. for 4 hours. After the incubation is complete each sample was vortex mixed again for 10 seconds and centrifuged at 10,000 rpm for 5 minutes in a Brinkmann Eppendorf 5415 centrifuge or equivalent. The top plasma layer was removed and transferred via a glass Pasteur pipette to a test tube.

An aliquot of the plasma was assayed for hemoglobin concentration using a modified version of Sigma's Drabkin's test kit. Plasma levels of hemoglobin, determined after incubation of the CSA liposomes with rat whole blood for four hours and corrected for the control value, are presented in Table 4. For this test, lower concentrations (<0.5 mg/ml) of hemoglobin released represents preferred formulation candidates. It should be noted that for formulations with a molar ratio of CSA lower than 1, less CSA is available in the formulation for the proposed cyclophilin interactions thus results for these samples may be favorably biased.

TABLE 4

Hemoglobin Release Test for Liposomal Cyclosporin Formulation

| Liposomal Cyclosporin Formulation (PC:Chol:DMPG:CSA) | Type of PC | Sonicated or Homogenized | Hemoglobin Concentration in Plasma (mg/ml) |
|---|---|---|---|
| 26:1:3:1 | HSPC | homogenized | 0.05 |
| 28:1:3:1 | HSPC | homogenized | 0.01 |
| 30:1:3:1 | HSPC | homogenized | 0.00 |
| 32:1:3:1 | HSPC | homogenized | 0.07 |
| 34:1:3:1 | HSPC | homogenized | 0.13 |
| 36:1:3:1 | HSPC | homogenized | 0.19 |
| CSA in Cremophor EL | na | na | 2.08 |
| 35:1:5:1 | HSPC | sonicated | 2.22 |
| 24:1:3:1 | HSPC | sonicated | 1.55 |
| 24:1:3:0.67 | HSPC | sonicated | 1.09 |
| 24:1:3:0.5 | HSPC | sonicated | 0.33 |
| 19:3:1 | DSPC | sonicated | 0.34 |
| 20:0.25:3:2 | DSPC | sonicated | 16.18 |
| 35:1:5:1 | DSPC | sonicated | 9.92 |
| 20:0.5:3:1 | DSPC | sonicated | 4.27 |
| 24:1:3:1 | DSPC | sonicated | 3.51 |
| 20:0.5:3:1.5 | DSPC | sonicated | 3.20 |
| 35:1:3:1 | DSPC | sonicated | 0.20 |
| 40:1:3:1 | DSPC | sonicated | 0.17 |
| 30:1:3:1 | DSPC | sonicated | 0.07 |

The data in Table 4 demonstrates that for optimal liposomal CSA formulations, which range from 28–40:1:3:1 PC: cholesterol: DMPG:CSA, there is significant improvement in lower levels of hemoglobin released in plasma compared with CSA CreL. These improvements range from 10 fold improvement (35:1:3:1 DSPC:cholesterol:DMPG:CSA) to >200 fold improvement (30:1:3:1 HSPC:cholesterol:DMPG:CSA).

The preferred formulations however are shown by combining the criteria of Tables 1 & 2 which indicate that the following range of formulas would achieve the necessary whole blood stability and lower hemoglobin release: 28:1:3:1 to 40:1:3: 1. The preferred formulations being: 28:1:3:1, 30:1:3:1, 32:1:3:1, 34:1:3:1, 36:1:3:1, and 40:1:3:1 with HSPC used as the preferred phosphatidylcholine.

Although the specification has been disclosed and illustrated with reference to particular applications, the principles involved are susceptible to numerous other applications which will be apparent to those skilled in the art. The invention is, therefore, to be limited only as indicated by the scope of the appended claims.

I claim:

1. Liposomes comprising a phosphatidylcholine, cholesterol, dimyristoylphosphatidylglycerol and cyclosporin wherein said liposomes are unilamellar having a size of less than 75 nanometers and are stable in whole mammal blood.

2. The liposomes as recited in claim 1 wherein the phosphatidylcholine is selected from the group consisting of distearoylphosphatidylcholine and hydrogenated soy phosphatidylcholine.

3. The liposomes as recited in claim 2 wherein the phosphatidylcholine is hydrogenated soy phosphatidylcholine.

4. The liposomes of claim 1 wherein the mole ratio of phosphatidylcholine to cholesterol to dimyristoylphosphatidylglycerol to cyclosporin ranges from about 28:1:3:1 to about 40:1:3:1.

5. The liposomes of claim 2 wherein the mole ratio of phosphatidylcholine to cholesterol to dimyristoylphosphatidylglycerol to cyclosporin ranges from about 28:1:3:1 to about 40:1:3:1. is about.

6. The liposomes of claim 3 wherein the mole ratio of phosphatidylcholine to cholesterol to dimyristoylphosphatidylglycerol to cyclosporin ranges from about 28:1:3:1 to about 40:1:3:1.

7. The liposomes of claim 1 wherein the mole ratio of phosphatidylcholine to cholesterol to dimyristoylphosphatidylglycerol to cyclosporin is about 30:1:3:1.

8. The liposomes of claim 2 wherein the mole ratio of phosphatidylcholine to cholesterol to dimyristoylphosphatidylglycerol to cyclosporin is about 30:1:3:1.

9. The liposomes of claim 3 wherein the mole ratio of phosphatidylcholine to cholesterol to dimyristoylphosphatidylcerol to cyclosporin is about 30:1:3:1.

* * * * *